US012616552B2

(12) United States Patent
Blomè et al.

(10) Patent No.: US 12,616,552 B2
(45) Date of Patent: May 5, 2026

(54) MARKER UNIT FOR USE IN AR AIDED SURGERY

(71) Applicant: Navari Surgical AB, Gothenburg (SE)

(72) Inventors: Axel Blomè, Gothenburg (SE); Carl Bodin, Västra Frölunda (SE); Christian Al-Maleh, Bohus (SE); Klas Modin, Gothenburg (SE); Lisa Månsson, Hindås (SE); Madeleine Gustavsson, Kungsbacka (SE); Mårten Falkenberg, Gothenburg (SE); Niclas Kvarnström, Kållered (SE); Torbjörn Lundh, Billdal (SE)

(73) Assignee: Navari Surgical AB, Gothenburg (SE)

( * ) Notice: Subject to any disclaimer, the term of this patent is extended or adjusted under 35 U.S.C. 154(b) by 0 days.

(21) Appl. No.: 18/840,431

(22) PCT Filed: Feb. 22, 2023

(86) PCT No.: PCT/EP2023/054443
§ 371 (c)(1),
(2) Date: Aug. 21, 2024

(87) PCT Pub. No.: WO2023/161286
PCT Pub. Date: Aug. 31, 2023

(65) Prior Publication Data
US 2025/0160997 A1 May 22, 2025

(30) Foreign Application Priority Data
Feb. 25, 2022 (SE) .................................... 2250262-9

(51) Int. Cl.
*A61B 90/00* (2016.01)
(52) U.S. Cl.
CPC ........ *A61B 90/39* (2016.02); *A61B 2090/365* (2016.02); *A61B 2090/3937* (2016.02);
(Continued)

(58) Field of Classification Search
CPC ............ A61B 90/39; A61B 2090/3937; A61B 2090/3966; A61B 2090/3995
See application file for complete search history.

(56) References Cited

U.S. PATENT DOCUMENTS 9,462,797 B2 * 10/2016 Kirkpatrick ............... A01L 3/00
9,474,888 B2 * 10/2016 Wiley ............... A61M 39/0208
(Continued)

FOREIGN PATENT DOCUMENTS

EP 1415609 A1 5/2004
WO WO-2016012556 A1 1/2016
(Continued)

OTHER PUBLICATIONS

PCT International Search Report and Written Opinion for PCT/EP2023/054443 that is the parent application to the instant application; dated Apr. 28, 2023; 14 pages.
(Continued)

*Primary Examiner* — Angela M Hoffa
(74) *Attorney, Agent, or Firm* — Harness, Dickey & Pierce, P.L.C.; Anthony G. Fussner

(57) ABSTRACT

Disclosed is a marker unit for use in augmented reality aided surgery, and in particular laparoscopic liver surgery. The marker unit comprises a flat body with two main surfaces. One of the main surfaces is provided with a set of optically detectable markers, and the opposite main surface is arranged to be connected to a bodily organ, and preferably provided with an adhesive. The marker unit further comprises a set of radiopaque markers that are visible by a medical imaging system. Both the optically detectable markers and the radiopaque markers are provided in a geometrical pattern not having rotational symmetry, thereby allowing the rotational position of the marker unit to be determinable. The geometrical patterns of the optically detectable markers
(Continued)

and the radiopaque markers have a fixed, predetermined correlation.

14 Claims, 4 Drawing Sheets

(52) U.S. Cl.
CPC ................. *A61B 2090/3966* (2016.02); *A61B 2090/3995* (2016.02)

(56) References Cited

U.S. PATENT DOCUMENTS

| | | | | |
|---|---|---|---|---|
| 10,265,512 | B2 * | 4/2019 | Wiley | ................. B29C 45/0053 |
| 10,806,541 | B2 * | 10/2020 | Ross | .................... A61B 6/4452 |
| 11,077,291 | B2 * | 8/2021 | Wiley | .............. A61M 39/0208 |
| 11,948,265 | B2 * | 4/2024 | Gibby | .................... G02B 27/01 |
| 12,053,247 | B1 * | 8/2024 | Chiou | .................... G06F 3/011 |
| 12,211,151 | B1 * | 1/2025 | Chiou | .................. G06T 19/003 |
| 12,288,306 | B2 * | 4/2025 | Gibby | .................... G06T 19/00 |
| 2010/0039506 | A1 | 2/2010 | Sarvestani et al. | |
| 2013/0338494 | A1 * | 12/2013 | Wiley | .............. A61M 39/0247 |
| | | | | 29/428 |
| 2014/0343405 | A1 | 11/2014 | Daon et al. | |
| 2015/0008004 | A1 * | 1/2015 | Kirkpatrick | .............. A01L 7/02 |
| | | | | 168/12 |
| 2017/0028185 | A1 * | 2/2017 | Wiley | ................. B29C 45/0053 |
| 2017/0064938 | A1 * | 3/2017 | Kirkpatrick | .............. A01L 7/02 |
| 2017/0354477 | A1 * | 12/2017 | Ross | .................... A61B 90/96 |
| 2018/0280092 | A1 | 10/2018 | Van Beek et al. | |
| 2018/0289444 | A1 | 10/2018 | Blair et al. | |
| 2018/0318035 | A1 | 11/2018 | Mclachlin et al. | |
| 2019/0159841 | A1 | 5/2019 | Abhari et al. | |
| 2019/0209080 | A1 | 7/2019 | Gullotti et al. | |
| 2019/0252603 | A1 * | 8/2019 | Wiley | .................... A61B 6/12 |
| 2019/0348169 | A1 | 11/2019 | Gibby et al. | |
| 2020/0005473 | A1 | 1/2020 | Yu | |
| 2020/0100847 | A1 | 4/2020 | Siegler et al. | |
| 2020/0163723 | A1 | 5/2020 | Wolf et al. | |
| 2020/0330180 | A1 | 10/2020 | Olive et al. | |
| 2021/0161614 | A1 * | 6/2021 | Elimelech | .............. A61B 34/20 |
| 2021/0353926 | A1 * | 11/2021 | Wiley | .................... B29C 65/08 |
| 2022/0008141 | A1 | 1/2022 | Chopra et al. | |
| 2023/0149116 | A1 * | 5/2023 | Stauffer | ................. G16H 20/40 |
| | | | | 606/102 |
| 2023/0169740 | A1 * | 6/2023 | Gibby | ................. G02B 27/017 |
| | | | | 345/619 |
| 2025/0061672 | A1 * | 2/2025 | Gibby | .................. G06T 7/0012 |
| 2025/0278913 | A1 * | 9/2025 | Gibby | .................... G06T 19/00 |

FOREIGN PATENT DOCUMENTS

| | | |
|---|---|---|
| WO | WO-2016170372 A1 | 10/2016 |
| WO | WO-2021146357 A1 | 7/2021 |
| WO | WO-2021216516 A1 | 10/2021 |

OTHER PUBLICATIONS

Teatini et al; The effect of intraoperative imaging on surgical navigation for laparoscopic liver resection surgery; www.nature.com/scientificreports; 2019; 11 pages.

Falkenberg et al.; Radiopaque Fiducials Guiding Laparoscopic Resection of Liver Tumors; 222.surgical-laparoscopy.com; vol. 32, No. 1, Feb. 2022; 5 pages.

Swedish Office Action for Swedish App. No. 2250262-9 that is a parent application to the instant application; Dated Sep. 23, 2022; 8 pages.

Swedish Office Action for Swedish Application No. 2250262-9 that is a parent application to the instant application; dated Nov. 16, 2023; 7 pages.

Swedish Office Action for Swedish application No. 2250262-9 that is a parent application to the instant application; Feb. 25, 2025; 9 pages.

* cited by examiner

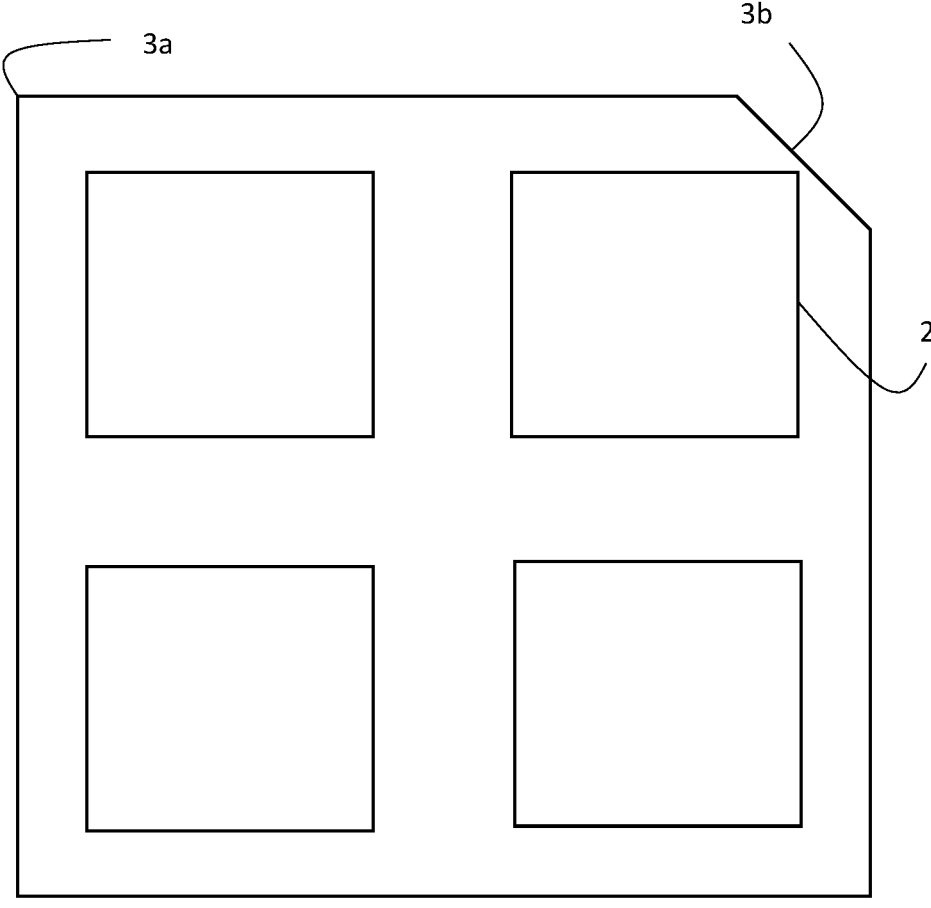
Fig. 5
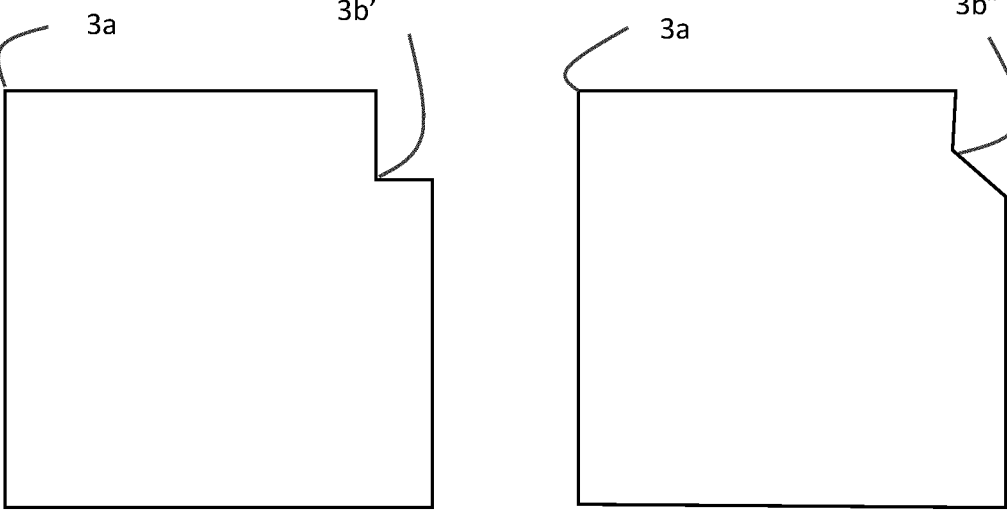
Fig. 6                                        Fig. 7

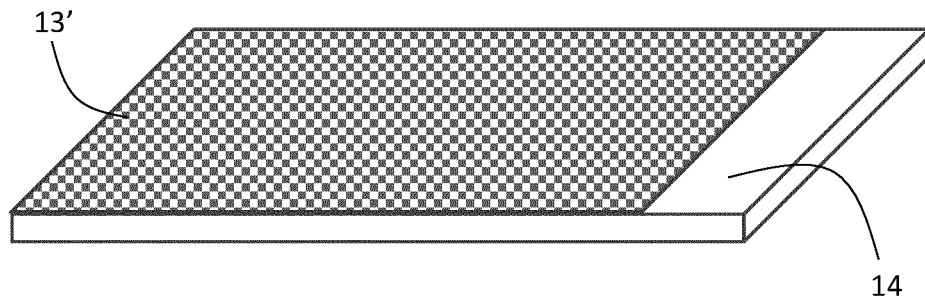
Fig. 8
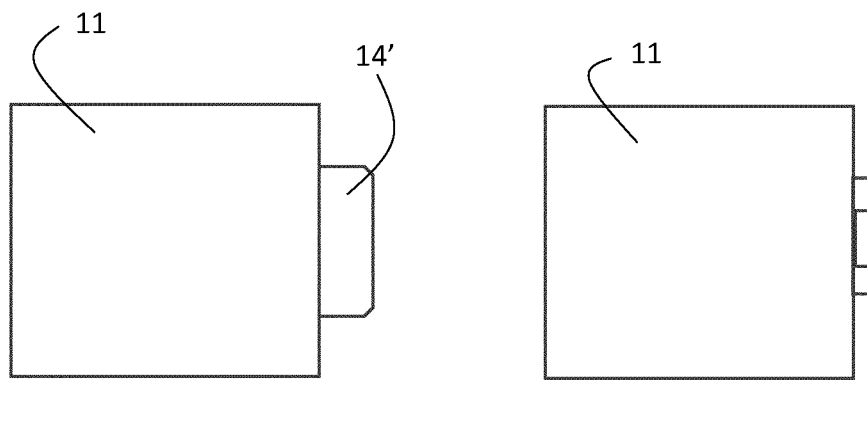
Fig. 9                    Fig. 10
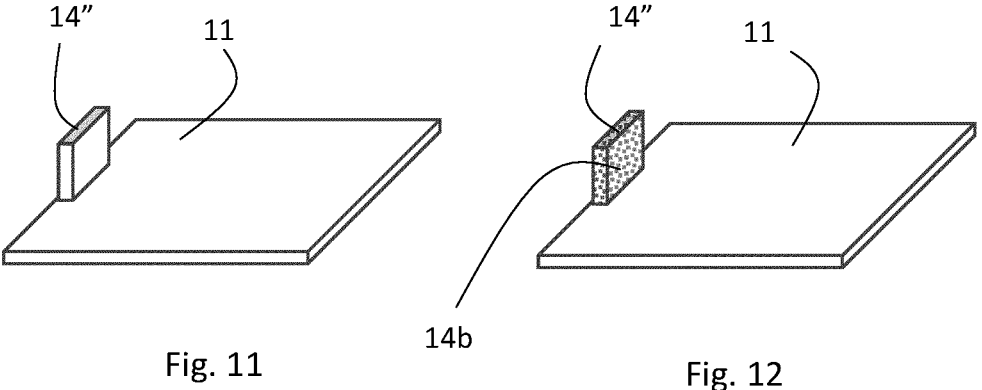
Fig. 11                    Fig. 12

MARKER UNIT FOR USE IN AR AIDED SURGERY

This patent application is a U.S. national stage filing under 35 U.S.C. § 371 of PCT International Application No. PCT/EP2023/05443 filed Feb. 22, 2023 (published as WO2023/161286 on Aug. 31, 2023), which claims priority to and the benefit of Swedish Patent Application No. SE 2250262-9 filed Feb. 25, 2022. The entire contents of these applications are incorporated herein by reference.

TECHNICAL FIELD OF THE INVENTION

The present invention relates to a marker unit for use in augmented reality (AR) aided surgery. The invention also relates to a system for augmented reality (AR) aided surgery comprising such a marker unit.

BACKGROUND OF THE INVENTION

Surgical removal of a cancer tumor in the liver was traditionally done by open surgery. Today there is a big change towards laparoscopic, minimally invasive surgery. However, laparoscopic surgery is a relatively complicated procedure, and requires great skill and much training. In particular, it is often difficult for the surgeon to find his or her way and orient based on the limit visual input available from the laparoscopic camera. Liver surgery is particularly challenging, due to the uniformity of the liver's shape and surface. Furthermore, tumors in the liver are usually located deep inside the liver and not visible with the thin laparoscopic light-camera.

In laparoscopic surgery, a number of ports are provided, for access to the operation site with instruments, camera and the like. The surgeons orient themselves from the outside, creating a perception of the inside through the 2D-images from the camera and a preoperative 3D-image on the side as a map.

Although laparoscopic surgery has many advantages, it is a difficult technique to learn that needs a lot of practice. It is especially complicated with e.g. liver tumors, since the liver is an unusually homogeneous organ with a smooth surface, making it very hard for the surgeons to orient themselves in the 2D-camera view.

In recent years, many attempts have been made to overcome these problems. "Radiopaque fiducials guiding laparoscopic resection of liver tumours" by M. Falkenberg et al, Surg. Laparosc. Endosc. Percutan Tech, Sep. 28, 2021 investigates how radiopaque fiducials and fluoroscopy can complement ultrasound during tumor resection in the liver and provide augmented 3D-information of the liver combined with the information from the camera view. The overall aim of the study was to develop a workflow where the position of the tumor can be traced during the procedure as a complement to the use of ultrasound.

"The effect of intraoperative imaging on surgical navigation for laparoscopic liver resection surgery" by A. Teatini et al, Scientific Reports (2019) 9:18687 relates to the so-called CAScinationAR solution. It is based on cameras that detects markers outside the body. For this to work, the body and the liver have to be unmoved. Using that, and the information from the earlier taken CT-scan, gives the opportunity (in theory) to display hidden parts. However, in practice it is difficult to remain full stability between all the parts during surgery.

In addition, US20200005473 discloses alignment system for liver surgery, WO 2016/170372 discloses an apparatus and method for registering pre-operative image data with intraoperative laparoscopic ultrasound images, and WO 2016/012556 discloses an image generating apparatus method with combination of functional imaging and ultrasound image.

Despite these efforts, there is still a need for a more efficient system for guiding a surgeon during laparoscopic surgery, especially for liver surgery. In particular, there is a need for a system which facilitates orientation at the operation site, inside the body, and which can be implemented and used in a relatively fast and cost-efficient manner.

SUMMARY OF THE INVENTION

It is therefore an object of the present invention to provide a marker unit for use in augmented reality aided surgery, which alleviates all or at least some of the drawbacks of presently known systems. Another object of the invention is to provide a system for AR aided surgery comprising such a marker unit.

This object is achieved by means of a marker unit and a system for AR aided surgery as defined in the appended claims.

According to a first aspect of the invention, there is provided a marker unit for use in augmented reality aided surgery, the marker unit comprising a flat body with two main surfaces, one of the main surfaces being provided with a set of optically detectable markers and the opposite main surface being arranged to be connected to a bodily organ, and preferably provided with an adhesive, and further comprising a set of radiopaque markers, visible by a medical imaging system, wherein both the optically detectable markers and the radiopaque markers are provided in a geometrical pattern not having rotational symmetry, thereby allowing the rotational position of the marker unit to be determinable, and wherein the geometrical patterns of the optically detectable markers and the radiopaque markers have a fixed, predetermined geometrical correlation.

By medical imaging system is here meant a system for imaging the interior of a body. The medical imaging data is preferably 3D-data and is preferably obtained through a non-invasive procedure. In particular, the medical imaging system may be a medical X-ray or ultrasound system.

The optically detectable markers are detectable by detection of light from the visible spectrum, such as by a camera, and is preferably provided as 2D-data.

The present invention is based on the realization that a single marker unit, designed and structured in a certain way, enables correlation between medical image data and optically received data, such as from a laparoscopic camera. This correlation can be made in real time, enabling it to be presented to the user as an augmented reality view, showing both the images in combination.

The present marker units can be placed easily and securely, providing a quick and cost-efficient procedure. Further, since the sets of markers can be correlated directly from the images received from the medical imaging system and the optical detection system, such as a camera, there is no need to know the exact position of the medical imaging device or the camera, or any other external devices.

Even though more than one marker unit may be used, only a single marker unit would normally be sufficient to provide the required correlation between the images. Thus, it suffices to place a single marker unit on the anatomical part and surface where surgery is to be performed, such as on the surface of the liver. The marker unit comprises a set of optically detectable markers, which are detectable e.g. with an optical camera. Further, the marker unit comprises a set of radiopaque markers, visible by a medical imaging system, such as computed tomography (CT), cone beam computed tomography (CBCT), magnetic resonance imaging (MRI), and ultrasound (US) imaging. However, other medical imagining systems and techniques may also be used, as per se known in the art.

One side of the marker unit may be provided with an adhesive, making it very easy to fixate to the anatomical structure where it should be located, such as on the surface of a liver. Such fixation is non-invasive, and fixation can be made through the laparoscopic ports, quickly and efficiently.

Both the optically detectable markers and the radiopaque markers are provided in a geometrical pattern not having rotational symmetry, thereby allowing the rotational position of the marker unit to be determinable, and further the geometrical patterns of the optically detectable markers and the radiopaque markers have a fixed, predetermined correlation. This makes it possible to uniquely identify the exact position of the marker unit, in all directions, from both the medical imaging data and from the optically received data. Due to the known correlation between the marker sets, this then allows the images to be correlated, allowing them to be presented in a combined way, as augmented reality images.

Thus, the present invention provides a marker unit useable as a reference point, both for pre-operative three-dimensional (3D) image data of an organ, as well as for an optical reference point for e.g., a camera.

The flat body of the marker unit is preferably made of a rigid material. Consequently, the marker unit is preferably rigid. By rigid is here meant that the flat body, and the marker unit, will not deform during ordinary use and handling, and is difficult to bend with ordinary finger pressure. The rigidity of the flat body and marker unit ensures that the marker unit will not be deformed during use, and in particular when attached to the bodily organ, thereby ensuring that the reading and correlation of the sets of markers will remain unaffected.

In an embodiment, the flat body comprises two layers fixedly connected to each other, wherein the set of radiopaque markers is arranged sandwiched between said two layers. However, the flat body may alternatively comprise only a single layer, or three or more layers. Further, the radiopaque markers may alternatively be arranged on an outer surface of the flat body.

In an embodiment the flat body has a rectangular shape, and preferably a square shape. However, other shapes, such as a nearly rectangular shape but with rounded or beveled corners are also feasible. In other embodiments, the flat body may also be circular, oval, hexagonal, octagonal, etc.

In one embodiment, the flat body may comprise at least one layer made of a radiopaque material, such as a radiopaque plastic material, so-called X-ray plastic. For example, the flat body may comprise a single layer made of such a radiopaque material. In such embodiments, recognizable features e.g. at the edges may form the set of radiopaque markers. For example, the corners may serve as such recognizable features, and thereby form the set of radiopaque markers. At least one of the corners may then be shaped differently than the others, to make the pattern non-rotationally symmetric. For example, the differently shaped corner may be a cut corner, a corner with a cut-out indentation, a rounded corner, or the like.

The main surface may have dimensions in two orthogonal directions being in the range of 5-20 mm, and preferably in the range of 5-15 mm, and most preferably in the range of 7-12 mm. In case of a rectangular shape the dimensions may be seen as along the orthogonal sides.

In an embodiment, the marker unit may have a maximal extension in any direction of less than less than 12 mm, and preferably less than 10 mm. The maximal extension relates to the longest distance between any two positions of the marker unit. In a flat, circular arrangement, the maximal extension will essentially correspond to the diameter, whereas in a square or rectangular configuration, the maximal extension will essentially correspond to the extension of a diagonal line between two oppositely arranged corners. A marker unit having a maximal extension of less than 12 mm makes the marker unit highly advantageous for use in many laparoscopic surgical procedures, since laparoscopic ports often have an inner diameter of 12 mm. A marker unit having a maximal extension of less than 10 mm makes the marker unit even better suited for laparoscopic surgical procedures, since it may then be used both for laparoscopic ports having an inner diameter of 12 mm, and also for laparoscopic ports having an inner diameter of 10 mm, as is also commonly used.

The set of optically detectable markers preferably comprises a plurality of geometrical figures distributed over the main surface. The geometrical figures may e.g. be rect-angles. In an embodiment, the plurality of geometrical figures may comprise a plurality of QR codes. The QR codes may comprise black squares arranged in a square grid on a white background. The coloring may also be inverted, with white squares on a black background. However, other color combinations are also feasible, such as black squares on a red background, etc. The squares may comprise relatively larger position squares in three out of four corners, and optionally a relatively smaller alignment square in the fourth corner. Additional alignment squares may also be provided, such as at the sides between the squares at the corners, and/or in the center. Timing lines may also be provided between the squares at the corners. The QR codes may also comprise a data carrying pattern, but this is optional in the present context, and may be omitted.

However, other types of geometrical figures may also be used such as polygons, e.g. triangles, pentagons and hexagons, but also ellipses, circles, semicircles and other forms of circle sectors, etc.

The radiopaque markers may be formed of a metal or the like, as is per se known in the art. The set of radiopaque markers may e.g. be arranged as a grid of elliptical or rectangular dots, and with one or more of the positions being empty, thereby making the pattern non-rotationally symmetric.

However, the radiopaque markers may also be formed by detectable features on a layer or flat body formed by a radiopaque material, such as radiopaque plastic material. Such detectable features may e.g. be provided in the form of detectable and distinguishable corners of a generally rect-angular layer/body.

The main surface comprising the set of optically detectable markers is preferably hydrophobic. Hereby, it is avoided that water, bodily fluids, and the like, is assembled on the surface. This ensures that the optically detectable markers are not obscured during use. The main surface comprising the set of optically detectable markers is further preferably non-reflecting, which also makes optical detection easier.

The hydrophobic surface may be obtained by use of a coating or layer of hydrophobic material arranged on the main surface of the marker unit. However, alternatively, the marker unit may in itself be made by a hydrophobic material. The hydrophobic material preferably primarily comprises nonpolar molecules. The hydrophobic material is preferably such that aqueous liquids coming into contact with the hydrophobic material cluster together, forming micelles, and with a high contact angle relative the surface of the hydrophobic material, preferably exceeding 90 degrees, and more preferably exceeding 100 degrees, and most preferably exceeding 110 degrees. The contact angle may also exceed 145 degrees, in which case the hydrophobic material may be referred to as superhydrophobic.

The marker unit is particularly well suited for laparoscopic surgery, and in particular for laparoscopic liver surgery. The laparoscopic surgery may here be conventional, manually performed laparoscopic surgery, or robot assisted laparoscopic surgery. However, the marker unit may also be used for other types of laparoscopic surgery and endoscopic surgery, and also for other types of surgery where the direct optical visibility is limited.

The marker unit may comprise a handle. Such a handle may be provided in the form of a gripping or manipulation area formed on the marker unit. The gripping or manipulation area is preferably a part of the marker unit not provided with an adhesive. The gripping or manipulation area is also preferably arranged outside the bounds of the optically detectable markers. Hereby, the marker unit may be gripped and manipulated by conventional laparoscopic tools and instruments, such as laparoscopic grippers, graspers, etc, without the risk of damaging the marker unit, or in other ways negatively affecting its properties, functionality and performance.

Additionally, or alternatively, a handle may be arranged as a protruding portion, arranged to protrude laterally or transversely in relation to the main surface of the marker unit. In one embodiment, the protruding portion may extend laterally, and preferably in the plane of the main surface of the marker unit. In another embodiment, the protruding portion may protrude transversely in relation to the main surface, such as in an orthogonal direction in relation to the main surface. The protruding portion may e.g. have width which is smaller than the width and length of the marker unit.

The handle may be provided with a friction increasing arrangement to increase the friction, thereby making it easier to grip and hold the marker unit, e.g. with a laparoscopic tool. The friction increasing arrangement may e.g. comprise a surface texture on a surface of the handle, e.g. in the form of corrugations. Additionally, or alternatively, the friction increasing arrangement may comprise a coating of a high friction material, etc.

According to another aspect of the invention, there is provided a system for augmented reality aided surgery comprising a marker unit as discussed in the foregoing, and further comprising a display and a controller, the controller being arranged to:

receive medical imaging data showing the marker unit at a position intended for surgery;

receive optically received image data showing the marker at the position intended for the surgery;

correlate the medical imaging data and the optically received image data based on the position of the set of radiopaque markers in the medical imaging data and the set of optically detectable markers in the optically received image data;

providing an augmented reality image on the display, the augmented reality image comprising at least in part image data from the medical imaging data and the optically received image data.

The medical imaging data may be received from at least one of: computed tomography scan (CT), cone beam computed tomography (CBCT), magnetic resonance imaging (MRI), and ultrasound imaging (US).

The optically received image data is preferably received from a camera, and preferably a laparoscopic camera.

With this aspect of the invention, similar advantages and preferred features are present as in the previously discussed first aspect of the invention, and vice versa.

These and other features and advantages of the present invention will in the following be further clarified with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein:

FIG. 5 is a schematic illustration, in a planar top view, of a main surface of a marker unit having sets of optically detectable and radiopaque markers, in accordance with another embodiment of the invention;

FIGS. 6-7 are schematic illustration, in planar top views, of a main surface of a marker unit having sets of radiopaque markers, in accordance with other embodiments of the invention, FIG. 8 is a schematic perspective view of a marker unit with a handle, in accordance with an embodiment of the invention;

FIGS. 9-10 are schematic illustrations, in planar top view of marker unit with laterally protruding handles in accordance with other embodiments of the invention; and FIGS. 11-12 are schematic perspective views of marker units with transversely protruding handles in accordance with yet other embodiments of the invention.

DETAILED DESCRIPTION OF CURRENTLY PREFERRED EMBODIMENTS

In the following detailed description, preferred embodiments of the present invention will be described. However, it is to be understood that features of the different embodiments are exchangeable between the embodiments and may be combined in different ways, unless anything else is specifically indicated. Even though in the following description, numerous specific details are set forth to provide a more thorough understanding of the present invention, it will be apparent to one skilled in the art that the present invention may be practiced without these specific details. In other instances, well known constructions or functions are not described in detail, so as not to obscure the present invention. In the following examples, an embodiment related to laparoscopic liver surgery is disclosed. However, it is to be acknowledged by the skilled reader that the method and system are correspondingly useable in many other types of surgical procedures.

Figure 1:
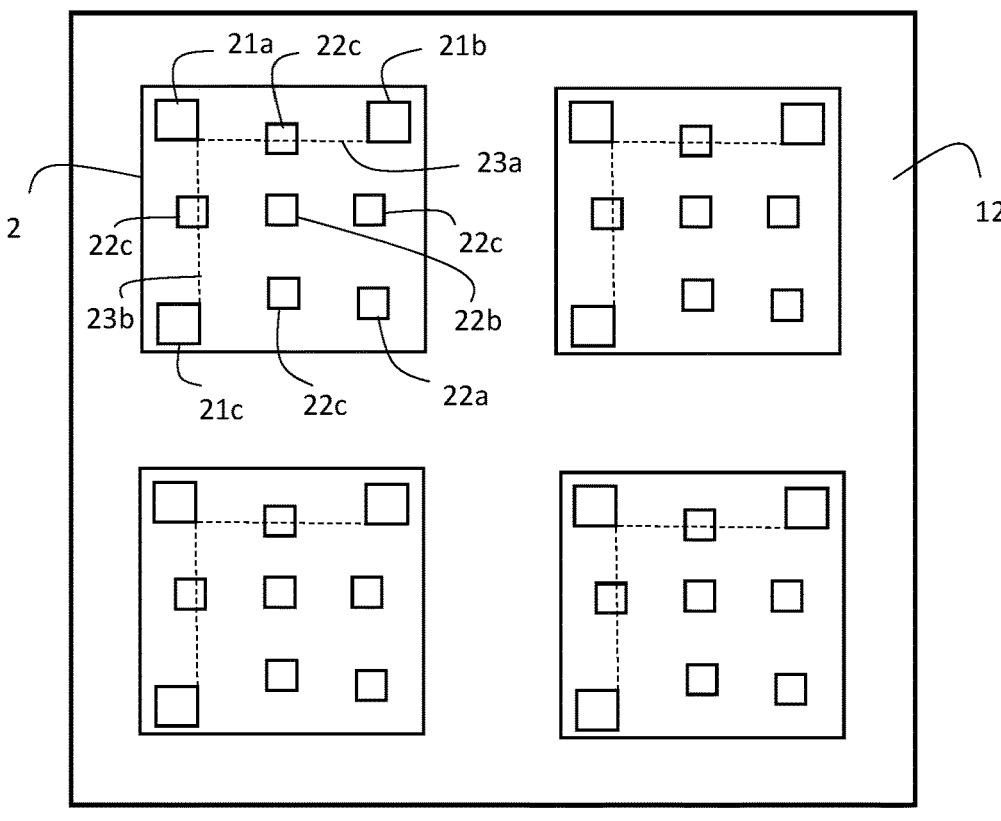
FIG. 1 is a schematic illustration, in a planar top view, of a main surface of a marker unit having a set of optically detectable markers, in accordance with an embodiment of the invention.
Figure 2:
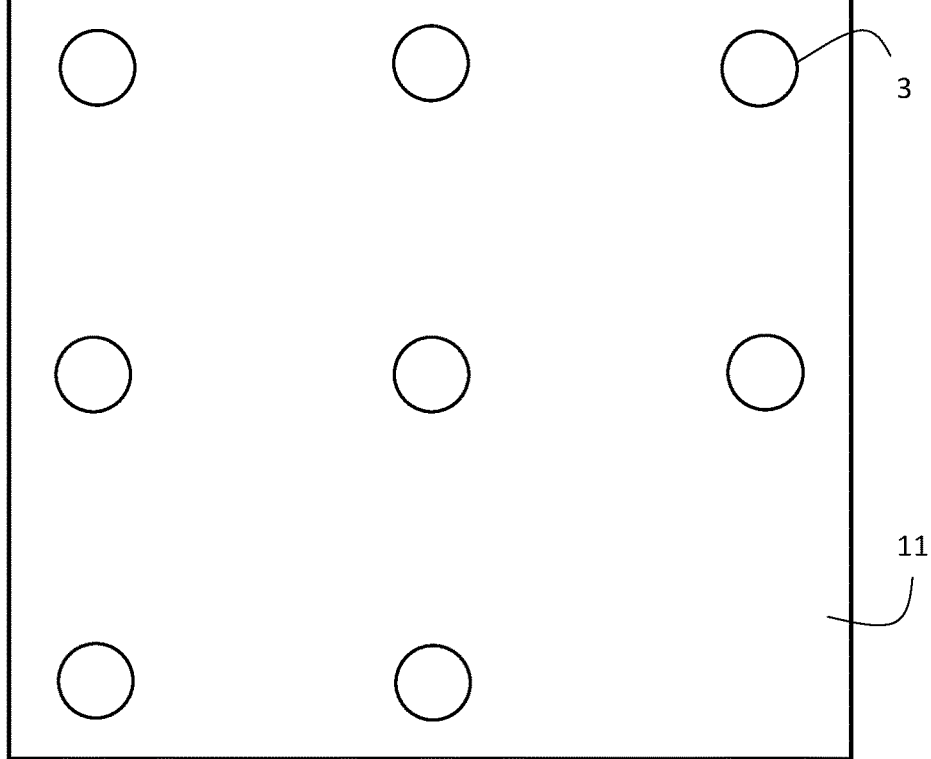
FIG. 2 is a schematic illustration, in a planar top view and with the upper layer removed or made invisible, of a bottom layer of the marker unit of FIG. 1 having a set of radiopaque markers, in accordance with an embodiment of the invention.
Figure 3:
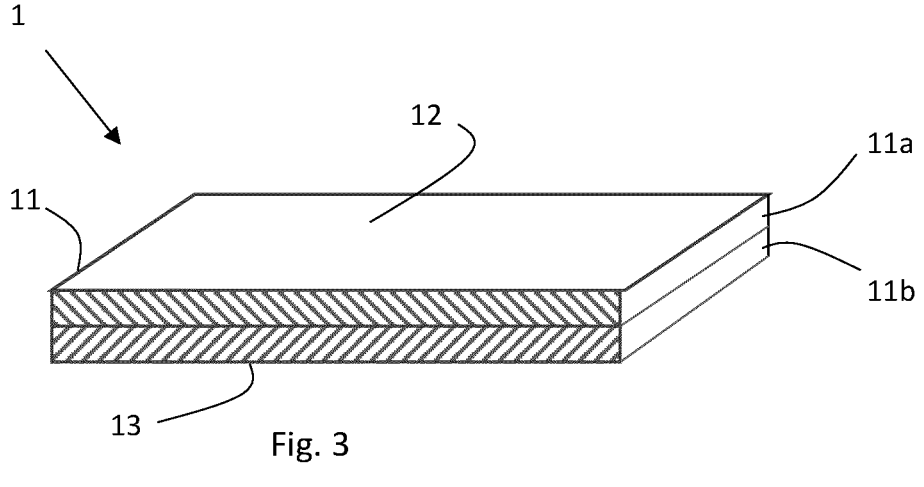
FIG. 3 is a schematic perspective view of a marker unit in accordance with the invention.

A marker unit 1 will first be discussed, with reference to FIGS. 1-3. The marker unit comprises a flat body 11, preferably formed of a relatively rigid plastic material. The material is preferably biocompatible and heat resistant to at least 100 deg. C. The flat body may comprise two layers 11*a*, 11*b* fixedly connected to each other, e.g. with adhesive.

The flat body has two main surfaces 12, 13 on opposite sides, and a sidewall around the circumference. The flat body, and as a consequence the main surfaces, here have a rectangular shape, and in particular a generally square shape. However, other shapes, such as a nearly rectangular shape but with rounded or beveled corners are also feasible. In other embodiments, the flat body may also be circular, oval, hexagonal, octagonal, or in the form of other polygons, etc. In one embodiment, the flat body has a polygonal shape.

The main surface may have dimensions in two orthogonal directions being in the range of 5-20 mm, and preferably in the range of 5-15 mm, and most preferably in the range of 7-12 mm. In case of a rectangular shape the dimensions may be seen as along the orthogonal sides. For example, the main surfaces may form a square with both sides being about 10 mm, forming an area of about 1 cm². The height of the marker unit is much smaller than the side dimensions. The height may e.g. be in the range of 1-5 mm, and preferably in the range 1-3 mm. Due to the limited size, the marker unit can easily be introduced into the body and to the surgery location through a laparoscopic port, discussed further below, without any need to fold or compress the marker unit for insertion. Thus, differently put, the marker unit is preferably dimensioned so that it can be introduced into a standard laparoscopic port.

On one of the main surfaces 12, there is a set of optically detectable markers, as will be discussed in more detail in the following.

On the other, opposite main surface 13, there may be provided an adhesive. The adhesive may be of any type suitable for connection to an anatomical body part, as is per se known in the art. For example, the adhesive may be a biodegradable adhesive, such as a fibrin adhesive agent. The adhesive may initially be covered by a cover liner, which may be removed prior to use to expose the adhesive. However, the adhesive may also be provided in other ways, such as initially being provided separately from the marker unit, to be arranged on a main surface of the marker unit prior to Insertion and fixation of the marker unit to a bodily organ.

Arranged integrated in the marker unit, and for example arranged between the layers 11*a* and 11*b*, there is provided a set of radiopaque markers, as will also be discussed in more detail in the following.

Both the optically detectable markers and the radiopaque markers are provided in a geometrical pattern not having rotational symmetry, thereby allowing the rotational position of the marker unit to be determinable, and further the geometrical patterns of the optically detectable markers and the radiopaque markers have a fixed, predetermined correlation. This makes it possible to uniquely identify the exact position of the marker unit, in all directions, from both medical imaging data and from optically received data. Due to the known correlation between the marker sets, this then allows the images to be correlated, allowing them to be presented in a combined way, as augmented reality images.

The set of optically detectable markers preferably comprises a plurality of geometrical figures distributed over the main surface. The geometrical figures may e.g. be rectangles.

In the present embodiment, the plurality of geometrical figures comprises a plurality of QR codes 2. The QR codes may comprise black squares arranged in a square grid on a white background. The squares may comprise relatively larger position squares 21*a-c* in three out of four corners, and optionally a relatively smaller alignment square 22*a* in the fourth corner. An additional alignment square 22*b* may also be provided in the center. Further, additional alignment squares 22*c* may be provided at the sides between the squares at the corners. So-called timing lines 23*a*, 23*b* may also be provided between the squares at the corners, and particularly between the position squares 21*a-c*. The QR codes may also comprise a data carrying pattern, but this is optional in the present context, and may be omitted.

However, it is also feasible to use only the position squares 21*a-c*, or in combination with only the alignment square 22*a*, or additionally or alternatively, one or more of the other alignment squares 22*b-c*.

The surface 12 of the marker unit may comprise a plurality of such QR codes. In the illustrative example, there is provided four QR codes 2, arranged in the four quadrants of the main surface. Since each marker unit comprises at least 3-4 OR codes, and since each QR code typically comprises 4 detectable squares, e.g. one in each corner of each QR code, this in total provides at least 12-16 detectable markers on the main surface of the marker unit. Additionally, or alternatively, the corners in themselves of the QR codes may serve as the optically detectable markers. Other geometrically distinct patterns or features of the main surface may also serve as the optically detectable markers.

The radiopaque markers may be formed of a metal or the like, as is per se known in the art. The set of radiopaque markers may e.g. be arranged as a grid of circular or rectangular dots 3, and with one or more of the positions being empty, thereby making the pattern non-rotationally symmetric. In the illustrative example, the markers 3 are provided in a 3×3 grid, but with the marker in the lower right corner being omitted. However, other non-rotational symmetric patterns are also feasible.

The two sets of markers, i.e. the optically detectable markers 2 and the radiopaque markers 3, have a fixed, predetermined geometric correlation. For example, the outer corner elements of both patterns may be overlying each other. For example, positioning square 21*a* in the upper left QR code 2 may be overlying the upper left marker 3, the positioning 21*b* in the upper right QR code may be overlying the upper right marker 3, and the positioning square 21*c* in the lower left QR code may be overlying the lower left marker 3. However, other ways of correlating the sets of markers to each other are also feasible.

The main surface comprising the set of optically detectable markers is preferably hydrophobic and non-reflective.

Other realizations of the optically detectable markers and/or the radiopaque markers are also feasible.

In one embodiment, illustrated in FIG. 5, the flat body may comprise at least one layer made of a radiopaque material, such as a radiopaque plastic material, so-called X-ray plastic. For example, the flat body may comprise a single layer made of such a radiopaque material. In such embodiments, recognizable features e.g. at the edges may form the set of radiopaque markers. For example, the corners may serve as such recognizable features, and thereby form the set of radiopaque markers 3*a-b*. At least one of the corners 3*b* may then be shaped differently than the others, to make the pattern non-rotationally symmetric. For example, the differently shaped corner 3*b* may be a cut corner.

The optically detectable markers 2 may here be provided as QR codes, in the same way as in the previously discussed embodiment. Alternatively, the optically detectable markers 2 may be other types of geometrically distinct shapes, such as rectangles. In one embodiment, the optically detectable markers 2 may also be provided by the shape of one or more of the layers of the flat body, such as corners or other distinct geometrical features of the shape.

In the illustrative embodiment of FIG. 5, one of the corners is cut, forming a blunt, beveled corner, thereby forming a distinct marker 3*b*. However, other ways of forming a distinct corner marker are also feasible. For example, as illustrated in FIG. 6, a distinct marker 3*b*' may be formed by cutting out a rectangular piece of the corner, thereby forming an inwardly pointing corner, in contrast to the outwardly pointing corners in the other corner positions. It is also possible to provide the cut-out with inclined sides, as in the illustrative example of FIG. 7, thereby forming a distinct marker 3*b*" having an inwardly pointing corner with a blunt or acute angle.

However, other distinct markers are also feasible, such as rounded cut-outs, etc. Cut-outs or the like may also be provided at other positions than at the corners, such as along one or more of the sides, or internally in the body/layer.

In the illustrative examples of FIGS. 5-7, only one of the markers 3*b*, 2*b*', 3*b*" is formed distinct from the remaining markers 3*a*. However, it is also possible to use two or more distinct markers, for example being provided with differently shaped cut-outs. Thus, two, three, four or more distinct radiopaque markers may be provided.

Figure 4:
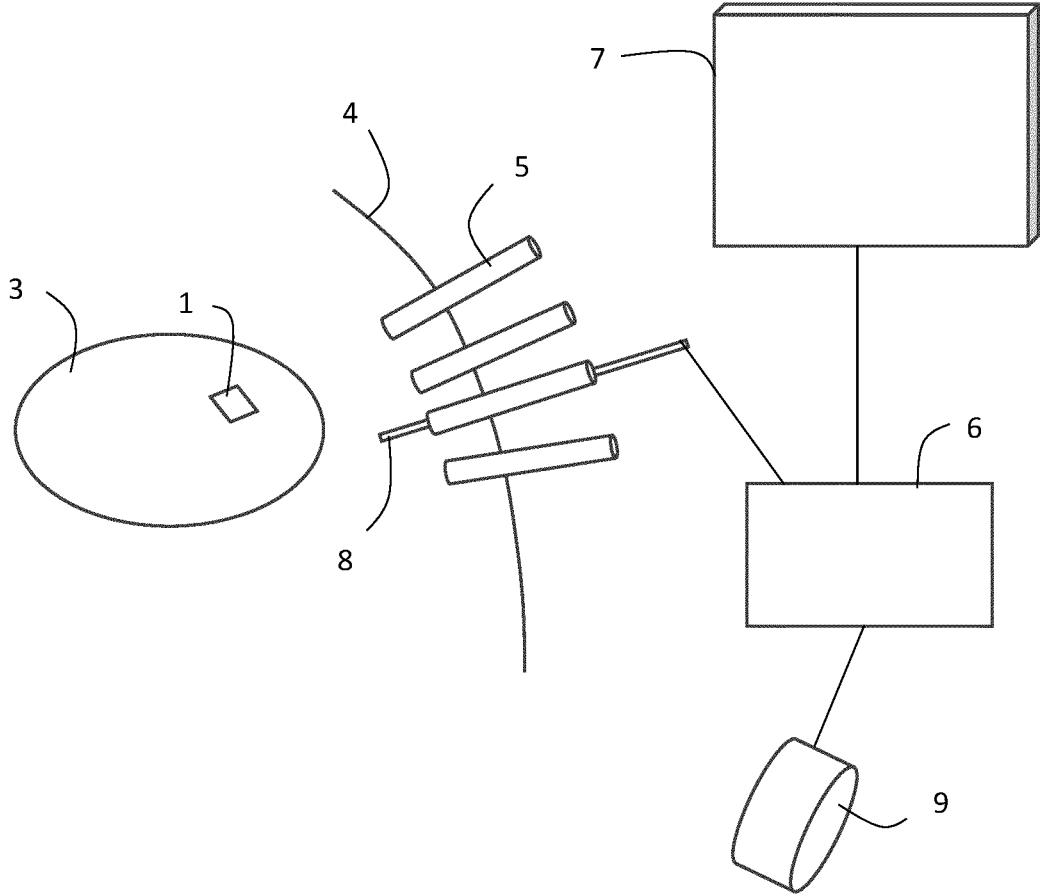
FIG. 4 is a schematic view of a system for augmented reality aided surgery, in accordance with an embodiment of the invention.

Next, a system for augmented reality aided surgery comprising the above-discussed marker unit will be discussed, with reference to FIG. 4.

The system comprises at least one marker unit 1, here positioned on a liver 3. Placement of the marker unit 1 may take place through a laparoscopic port 5, arranged through the skin 4 of the patient when inflated for surgery.

The system further comprises a controller 6, connected to the optical display 7. The controller is further connected to a medical imaging device/system 9, to receive medical imaging data. The medical imagining device may e.g. be a device/system for computed tomography (CT), cone beam computed tomography (CBCT), magnetic resonance imaging (MRI), or ultrasound (US) imaging. However, other medical imagining systems and techniques may also be used, as per se known in the art. The controller 6 is further connected to an optical imaging device/system, such as a laparoscopic camera 8.

The controller 6 is arranged to:

receive medical imaging data showing the marker unit at a position intended for surgery;

receive optically received image data showing the marker at the position intended for the surgery;

correlate the medical imaging data and the optically received image data based on the position of the set of radiopaque markers in the medical imaging data and the set of optically detectable markers in the optically received image data;

providing an augmented reality image on the display, the augmented reality image comprising at least in part image data from the medical imaging data and the optically received image data.

The controller can be realized on a personal computer, or other types of computers, but can also be realized on a tablet or the like.

The display may be the conventional display screen for the optical camera 8.

However, more than one display may be provided. Additionally, or alternatively, the display may be provided in the form of a worn display, such as integrated in glasses.

A method for using the system will now be discussed.

First, the patient is prepared for surgery. This typically means that the surgeon makes small incisions, attaches the laparoscopic ports and the abdominal cavity is inflated with carbon dioxide to give the surgeon more room to work.

Secondly, the marker unit is inserted through the laparoscopic port and is placed on the liver surface. Before introducing the marker unit, the adhesive is exposed by removing any liner or the like. When inserted, e.g. with laparoscopic forceps, it suffices to gently press the adhesive side of the marker unit towards the liver surface to obtain fixation. The marker unit is preferably arranged overlying, or close to, the position where a part of the liver is to be surgically removed. However, the marker unit may also be fixated to the bodily organ in other ways, such as by an externally provided adhesive, or by other per se known fixation members.

Fixated of the marker unit to the bodily is made in such a way that the main surface with the optically detectable markers faces away from the bodily organ, thereby exposing the optically detectable markers.

Thereafter, the marker unit is detected in relation to patient's anatomical geometry. This is made by medical imaging, such as with CT, CBCT, MRI, US, etc.

Then, the laparoscopic camera and instruments are inserted through the laparoscopic ports.

When the liver and the marker unit are located in the camera's view, the marker unit provides a reference point for the software and an augmented reality projection is shown on the surgeon's display. The augmented reality image displayed can e.g. comprise the live image data, in 2D, received from the camera, and with additional image information showing e.g. internal parts of the liver and in particular the tumor, based on the medical image data, which is in 3D, but may be projected to the 2D image.

In particular, the augmented reality view may complement the optical 2D image by features obtained from the medical imaging data, such as the target structure, e.g. the tumor, structures at risk, such as important blood vessels or nerves, specifically recognizable features, structures not visible due to being inside the organ and covered by tissue, etc.

The surgeon now performs a resection of the tumor and removes the tumor together with the marker unit. When the marker unit has been placed essentially over the tumor, the marker unit can remain attached to the piece of tissue/tumor that is removed.

In order to facilitate gripping and handling of the marker unit e.g. by laparoscopic tools, such as laparoscopic grippers and graspers, the marker unit may be provided with a handle. Such handles may be realized in various ways. Some exemplary embodiments of marker units having such handles will be discussed in the following, with reference to FIGS. 8-12.

The marker unit illustrated in FIG. 8 comprises a handle 14. The handle 14 is here provided in the form of a gripping or manipulation area formed on the marker unit. The gripping or manipulation area is here a part of the marker unit not provided with an adhesive 13'. The gripping or manipulation area is also preferably arranged outside the bounds of the optically detectable markers. Hereby, the marker unit may be gripped and manipulated by conventional laparoscopic tools, such as laparoscopic grippers, graspers, etc, without the risk of damaging the marker unit, or in other ways negatively affecting its properties, functionality and performance.

In the embodiment of FIGS. 9 and 10, the handle 14' is instead arranged as a protruding portion, arranged to protrude laterally from the flat body 11, generally in the main surface of the marker unit. The protruding portion may be formed as a tab or tongue, and may have a width and length much smaller than the width and length of the flat body 11. The handle may be generally solid, as schematically illustrated in FIG. 9, or be provided with an opening 14*a*, as schematically illustrated in FIG. 10. Such an opening 14*a* may facilitate gripping of the handle.

In the illustrative embodiment, the handle is arranged on a side of the flat body, and preferably essentially centrally on this side. However, other arrangements are also feasible. For example, the handle may instead be arranged at or close to a corner of the flat body 11.

The handle may alternatively be directed in other directions than laterally, in the plane of the main surface. Such embodiments are schematically illustrated in FIGS. 11 and 12. Here, the handles 14" are formed as protruding portions, protruding transversely in relation to the flat body 11 and main surface. In the illustrative example, the handles protrude essentially perpendicularly in relation to the flat body 11 and the main surface. However, the handles may alternatively protrude in other directions, such as in various slanted directions.

In the illustrative embodiment, the handle is arranged as a transversely protruding, flat tab extending along a side of the flat body 11. However, the handle may also be provided in other ways, such as being non flat, extending in a non-straight line, extending in other directions than along a side, etc.

The protruding portion may e.g. have width which is smaller than the width and length of the marker unit.

The handle may further be provided with a friction increasing arrangement to increase the friction, thereby making it easier to grip and hold the marker unit, e.g. with a laparoscopic tool. Such a handle 14" is illustrated schematically in FIG. 12. The friction increasing arrangement may e.g. comprise a surface texture on a surface of the handle, e.g. in the form of corrugations, dimples, etc. Additionally, or alternatively, the friction increasing arrangement may comprise a coating of a high friction material, etc.

In the above-discussed embodiments, the marker unit is provided with a single handle. However, it is also feasible to use more than one handle, such as two, three or more handles. For example, two handles may be arranged on two opposite sides, or alternatively on two adjacent sides.

The invention has now been described with reference to specific embodiments. However, several variations of the marker unit and the surgery system are feasible. For example, one or both the sets of radiopaque and optically detectable markers may be realized in other ways, forming other forms of non-rotationally symmetric patterns. Further, the correlation between the marker sets may be by arranging corner markers to be overlying each other, but other ways of geometrically correlating the sets are also feasible. The system may also use other types of medical imaging, other types of displays, etc. Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements.

The invention claimed is:

1. A marker unit for use in augmented reality aided laparoscopic surgery of a bodily organ, the marker unit being made of a rigid material and comprising:

a flat body with two main surfaces, one of the main surfaces being provided with a set of optically detectable markers and the opposite main surface being provided with an adhesive and arranged to be connected to the bodily organ; and a set of radiopaque markers visible by a medical imaging system;

wherein both the optically detectable markers and the radiopaque markers are provided in a geometrical pattern not having rotational symmetry, thereby allowing the rotational position of the marker unit to be determinable;

wherein the geometrical patterns of the optically detectable markers and the radiopaque markers have a fixed, predetermined correlation;

wherein the flat body comprises two layers fixedly connected to each other;

wherein the set of radiopaque markers is arranged sandwiched between said two layers;

wherein the main surface comprising the set of optically detectable markers is hydrophobic and non-reflecting; and wherein the main surfaces have dimensions in two orthogonal direction in the range of 5-20 mm.

2. The marker unit of claim 1, wherein the flat body has a polygonal shape.

3. Ther marker unit of claim 2, wherein the flat body has a generally rectangular shape or square shape.

4. The marker unit of claim 1, wherein the main surface has dimensions in two orthogonal directions in the range of 5-15 mm or 7-12 mm.

5. The marker unit of claim 1, wherein the set of optically detectable markers comprises a plurality of geometrical figures distributed over the main surface.

6. The marker unit of claim 5, wherein the plurality of geometrical figures comprises a plurality of QR codes.

7. The marker unit of claim 1, wherein a maximal extension in any direction in the marker unit is less than 12 mm or less than 10 mm.

8. The marker unit of claim 1, wherein the marker unit is rigid.

9. The marker unit of claim 1, further comprising a handle for a laparoscopic tool.

10. The marker unit of claim 9, wherein the handle is arranged on a part of the flat body being free of the adhesive and/or the optically detectable markers.

11. The marker unit of claim 9, wherein the handle comprises one or more protruding portions that protrude in a lateral and/or transverse direction in relation to the main surfaces of the flat body.

12. A system for augmented reality aided surgery comprising a marker unit in accordance with claim 1, and further comprising a display and a controller, the controller being arranged to:

receive medical imaging data showing the marker unit at a position intended for surgery;

receive optically received image data showing the marker at the position intended for the surgery;

correlate the medical imaging data and the optically received image data based on the position of the set of radiopaque markers in the medical imaging data and the set of optically detectable markers in the optically received image data; and providing an augmented reality image on the display, the augmented reality image comprising at least in part image data from the medical imaging data and the optically received image data.

13. The system of claim 12, wherein the medical imaging data is received form at least one of: computed tomography scan, cone beam computed tomography, magnetic resonance imaging, and ultrasound imaging.

14. The system of claim 12, wherein the optically received image data is received from a camera, and preferably a laparoscopic camera.

\* \* \* \* \*